(12) United States Patent
Ohara et al.

(10) Patent No.: US 7,067,314 B2
(45) Date of Patent: Jun. 27, 2006

(54) MONOCLONAL ANTIBODY, ITS IMMUNOREACTIVE FRAGMENT AND HYBRIDOMA

(75) Inventors: Takaaki Ohara, Kobe (JP); Kenji Yamashita, Takamatsu (JP); Tetsu Kakutani, Kakogawa (JP); Seishi Kyoizumi, Aki (JP)

(73) Assignee: Kaneka Corporation, Osaka (JP)

(*) Notice: Subject to any disclaimer, the term of this patent is extended or adjusted under 35 U.S.C. 154(b) by 581 days.

(21) Appl. No.: 10/172,986

(22) Filed: Jun. 18, 2002

(65) Prior Publication Data

US 2002/0197655 A1   Dec. 26, 2002

(30) Foreign Application Priority Data

Jun. 19, 2001   (JP)   ............................. 2001-184432

(51) Int. Cl.
*C12N 5/06* (2006.01)
*G01N 33/543* (2006.01)
*G07K 16/00* (2006.01)
*C12P 21/08* (2006.01)

(52) U.S. Cl. ...................... 435/326; 435/346; 436/518; 436/532; 530/388.1; 530/388.2; 530/387.9

(58) Field of Classification Search ............. 530/388.1, 530/388.2, 387.9; 435/326, 346; 436/518, 436/532
See application file for complete search history.

(56) References Cited

U.S. PATENT DOCUMENTS

| | | |
|---|---|---|
| 4,714,680 A | 12/1987 | Civin |
| 5,061,620 A | 10/1991 | Tsukamoto et al. |
| 5,130,144 A | 7/1992 | Civin |
| 5,843,633 A | 12/1998 | Yin et al. |
| 6,127,135 A | 10/2000 | Hill et al. |

FOREIGN PATENT DOCUMENTS

| | | |
|---|---|---|
| EP | 0 662 512 A2 | 7/1995 |
| WO | WO 98/00523 A | 1/1998 |
| WO | WO 02/102837 A2 | 12/2002 |

OTHER PUBLICATIONS

Kumar et al ., Biotechnol Bioeng, 2001, V.75, pp. 570-580.*

* cited by examiner

*Primary Examiner*—Christina Chan
*Assistant Examiner*—Michail Belyavskyi
(74) *Attorney, Agent, or Firm*—Sughrue Mion, PLLC

(57) ABSTRACT

It is an object to utilize a novel HSCA-3 antigen occurring in immature hemopoietic stem cells and a monoclonal antibody recognizing said antigen in 1) the immunoassay or flow cytometry involving antibody labeling and 2) the isolation and purification of immature hemopoietic stem cells from human bone marrow cells, umbilical code blood or blood enriched in human hemopoietic stem cells by mobilization with G-CSF.

It is directed to a novel HSCA-3 antigen occurring in immature hemopoietic stem cells and to a monoclonal antibody or an immunoreactive fragment thereof which recognizes said antigen.

10 Claims, 4 Drawing Sheets

1. CD34 (Class III) antibody
2. HSCA-3 antibody 1  2

(A)

(B)

(C)

US 7,067,314 B2

MONOCLONAL ANTIBODY, ITS IMMUNOREACTIVE FRAGMENT AND HYBRIDOMA

FIELD OF THE INVENTION

The present invention relates to a novel HSCA-3 antigen, which occurs in CD34-positive (CD34$^+$; the like description applies to this CD antigen-positive cells hereinafter) hemopoietic stem cells and is a protein having a molecular weight of about 110×10$^3$ and to an HSCA-3 monoclonal antibody (hereinafter referred to as HSCA-3 antibody) which recognizes said antigen. The HSCA-3 antibody according to the invention can be utilized 1) in an immunoassay or flow cytometry involving antibody labeling and 2) the isolation and purification of immature hemopoietic stem cells from human bone marrow cells, umbilical cord blood, or blood enriched in human hemopoietic stem cells by mobilization with G-CSF.

BACKGROUND OF THE INVENTION

As a surface antigen marker of human hemopoietic stem cells and hemopoietic progenitor cells, the CD34 molecule is known (U.S. Pat. No. 4,714,680). The CD34 molecule is a cell-surface antigen expressed in undifferentiated cells of human bone marrow, and in view of the fact that the transplantation of purified CD34$^+$ cells results in rapid reorganization of blood cells in all systems and that proportion of the CD34$^+$ cell is well correlated with the result of a colony assay which is most prevalently used in the identification of hemopoietic stem cells (Nara Nobuo, Hematology, 2$^{nd}$ Edition, Bunkōdo (1995), pp. 1558), it is generally believed that hemopoietic stem cells are present in the CD34$^+$ cell fraction. The CD34 molecule is the earliest marker protein in hemopoietic progenitor cells. The CD34 molecule is a Type I transmembrane cell-surface glycoprotein having a molecular weight of 105×10$^3$ to 120×10$^3$. As a surface antigen marker of human hemopoietic stem cells which is similar to said CD34 molecule, the AC133 molecule is also known (U.S. Pat. No. 5,843,633). The antibody against AC133 molecule is said to react with 20 to 60% of CD34$^+$ cells and with all undifferentiated CD34$^+$ cells. This is a 5-transmembrane cell-surface glycoprotein with a molecular weight of 117×10$^3$. In addition, the CD90 molecule is also known to be a surface antigen marker of human hemopoietic stem cells (U.S. Pat. No. 5,061,620). The above are major proteins known as surface antigen markers of human hemopoietic stem cells; thus, only a few are known.

OBJECT OF THE INVENTION

The object of the present invention is to utilize a novel HSCA-3 antigen occurring in immature hemopoietic stem cells and a monoclonal antibody recognizing said antigen in 1) the immunoassay or flow cytometry involving antibody labeling and 2) the isolation and purification of immature hemopoietic stem cells from human bone marrow cells, umbilical cord blood or blood enriched in human hemopoietic stem cells by mobilization with G-CSF.

SUMMARY OF THE INVENTION

The inventors of the present invention discovered that a monoclonal antibody prepared by immunizing BALB/c mice with KG-1 cells recognizes the novel HSCA-3 antigen, and after an intensive investigation made to accomplish the above object, demonstrated that this antibody is capable of accomplishing the object. The present invention has been developed on the basis of the above finding.

The present invention, therefore, is directed to a monoclonal antibody or an immunoreactive fragment thereof
which recognizes human immature hemopoietic stem cells but does not recognize CD34$^+$ Jurkat cells. The invention is further directed to a solid support
comprising said monoclonal antibody or immunoreactive fragment as immobilized thereon.

The present invention is further directed to a hybridoma
characterized by its producing a monoclonal antibody
which recognizes human immature hemopoietic stem cells but does not recognize CD34$^+$ Jurkat cells
or a hybridoma
which is acquired by the fusion of antibody-producing cells of a mammal immunized with KG-1 cells,
which are human myeloblastoid cells derived from an acute myeloid leukemia patient, to myeloma cells.

In a still further aspect, the present invention is directed to the HSCA-3 antigen
which is a protein having a molecular weight of about 110×10$^3$ and
occurs in CD34$^+$ hemopoietic stem cells.

The present invention is further directed to a method of assaying the above-mentioned antigen
which comprises using said antibody or immunoreactive fragment in an immunoassay or flow cytometry involving fluorescent labeling, radioisotope labeling or enzyme labeling.

The invention is further directed to a method of isolating and purifying immature hemopoietic stem cells from human bone marrow cells, umbilical cord blood, or blood enriched in human hemopoietic stem cells with G-CSF, which comprises using said antibody or immunoreactive fragment.

DETAILED DESCRIPTION OF THE INVENTION

Figure 1:
FIG. 1 is an autoradiography chart showing an immunoprecipitation analysis of the HSCA-3 antibody-reactive antigen.

The present invention is now described in detail.

In the present invention, the methods for preparation and analysis of a monoclonal antibody which are known in the art are employed unless otherwise indicated.

The various terms used in this specification to describe the present invention are now explained.

The "HSCA-3 antigen" means a novel antigen which occurs in human hemopoietic stem cells and is a protein having a molecular weight of about 110×10$^3$.

The term "HSCA-3 antibody" means a monoclonal antibody which recognizes said HSCA-3 antigen. The HSCA-3 antibody is a monoclonal antibody produced by a hybridoma which is acquired by the fusion of spleen cells of a mammal immunized with KG-1 cells, which are human myeloblastoid cells derived from an acute myeloid leukemia patient, to myeloma cells.

The term "hemopoietic stem cells" means pluripotent cells which have an ability of differentiation into all kinds of blood cells, such as erythrocytes, leukocytes, megakaryocytes, etc., inclusive of lymphoid cells such as T cells and B cells, and which are capable of self-proliferation. Hemopoietic stem cells are characteristically CD34 antigen-positive and CD38 antigen-negative ($CD34^+$ $CD38^{31}$ ; the like description applies hereinafter to the corresponding CD antigen-positive and antigen-negative cells).

The present invention is now described in further detail.

The hybridoma which produces the monoclonal antibody of the invention can be prepared basically by applying a routine immunization procedure using KG-1 cells as a sensitizing antigen, then a cell fusion procedure using a routine cell fusion technique, and a cloning procedure using a routine cloning technique.

More particularly, using a non-human animal, such as the mouse, rat, rabbit, guinea pig, sheep, goat or chicken, as the animal to be immunized, KG-1 cells as the sensitizing antigen are administered intraperitoneally, subcutaneously or to the footpad, for example. Since the myeloma cells for use as the counterpart cell for a cell fusion are generally derived from mice, it is particularly preferable to immunize mice. This immunization is preferably carried out in a general method, for example, a method comprising administering a suitable dose of said KG-1 cells, as diluted and suspended in PBS(−) (phosphate-buffered saline, pH 7.2), physiological saline or the like, to recipient animals on a weekly basis for 1 to 3 months.

From the immunized animals, spleen cells, lymphocytes, peripheral blood or other antibody-producing cells are harvested and subjected to cell fusion with myeloma cells, which are a tumor cell line, to prepare hybridoma cells. As the antibody-producing cells, cells from the spleen excised after the last administration of KG-1 cells are preferably used. As the myeloma cells, the known cell lines, such as P3-NSI/1-Ag4-1 cells (briefly, NS-1 cells) (Kaehler et al., Eur. J. Immunol., 6:511 (1976)), SP2/0-Ag14 cells (briefly, SP2 cells) (Schulman et al., Nature, 276:269 (1978)), and FO cells (deSaint Groth et al., J. Immunol. Meth., 35:1 (1980)) are generally used. In order to facilitate acquisition of the objective antibody from a culture supernatant of the hybridoma, a myeloma cell line which does not secrete the inherent immunoglobulin in myeloma cells is preferably used. In this sense, NS-1 cells are preferred.

The cell fusion between an antibody-producing cell and a myeloma cell can be achieved by the routine procedure, for example in accordance with the protocol used by Kaehler and Milstein who performed a cell fusion for the first time in the world (Kaehler et al., Nature, 256;495 (1975)).

More particularly, this procedure is carried out in an ordinary nutrient medium in the presence of a fusion promoter. As the fusion promoter, polyethylene glycol (PEG) or Sendai virus, for example, is used. The cell fusion is carried out using antibody-producing cells and myeloma cells in a predetermined ratio, for example about 1 to 10:1. As the medium for cell fusion, a medium favorable for growth of myeloma cells, for example RPMI 1640 medium, can be mentioned as an example. In such a medium, the two kinds of cells are admixed, and a solution of polyethylene glycol (for example, one having an average molecular weight of 1,000 to 6,000) maintained at 37° C. is added in a concentration of 30 to 60% (w/v) with stirring to initiate cell fusion.

Further, a suitable medium is added and the centrifugal removal of the supernatant is repeated to recover the objective hybridoma.

This hybridoma is selected by culture in an ordinary selection medium, such as HAT medium which contains hypoxanthine (H), aminopterin (A) and thymidine (T). Culture in this HAT medium is continued for several days to a few weeks until cells other than the objective hybridoma have been killed. When it has become possible to confirm colonies of the hybridoma, a screening is carried out for the antibody in the culture supernatant. This screening for the antibody in the culture supernatant can, for example, be achieved by assaying the antibody activity in the culture supernatant by an ELISA technique using immobilized cells as the antigen (Ando Tamie et al., Introduction to Monoclonal Antibody Experiment Protocols, Kōdansha Scientific (1993), pp. 126). The hybridoma producing the objective antibody as selected by the above screening can be ultimately obtained as a colony comprising a single hybridoma clone by repeating the routine limiting dilution method.

The thus-obtained hybridoma producing the monoclonal antibody of the invention, like the ordinary hybridomas, can be cultured and subcultured using the known medium, such as RPMI 1640 or Dulbecco's modified medium. Moreover, it can be preserved for a long time in liquid nitrogen.

Further, by culturing the hybridoma of the invention in 15% fetal calf serum (FCS)-RPMI 1640 on a large scale, the monoclonal antibody of the invention can be prepared from the culture supernatant. As an alternative, the monoclonal antibody of the invention can be prepared from the ascites produced by injecting the hybridoma intraperitoneally to mice.

The monoclonal antibody thus prepared may be purified by the ordinary antibody purification technology. The antibody purification technology comprises precipitation (salting-out) with ammonium sulfate or the like, ion exchange chromatography using a diethylamino-ester (DEAE) derivative, a carboxymethyl (CM) derivative, or the like, hydroxyapatite chromatography, gel filtration chromatography, and affinity chromatography using Protein A or Protein G, among others. The purification of the monoclonal antibody may be made by using these techniques in combination.

The immunoglobulin class of the monoclonal antibody of the invention which can be obtained in the above manner is not particularly restricted but immunoglobulin (hereinafter abbreviated as Ig) G1 and kappa chain can be mentioned among others.

Even the Fab, $F(ab')_2$ and other immunoreactive fragments of the antibody, which can be obtained by digesting the monoclonal antibody of the invention with a proteolytic enzyme which does not decompose the antigen-binding site (Fab), such as papain, pepsin or the like, and isolating and purifying the protein in the routine manner, can be used in the same way as the monoclonal antibody of the invention insofar as they retain properties similar to those of said monoclonal antibody.

The antigen can be detected by the procedure in which the monoclonal antibody of the invention is reacted with the antigen and further with, as a secondary antibody, a labeled immunoglobulin as labeled with a fluorescent labeling material, such as fluorescein isothiocyanate (FITC), a radioisotope, such as $^{125}I$, or an enzyme, such as alkaline phosphatase or peroxidase. Moreover, the antigen can also be detected by labeling the very monoclonal antibody of the invention itself with a fluorescent labeling material, e.g. FITC, a radioisotope, e.g. $^{125}$I, or an enzyme, e.g. alkaline phosphatase or peroxidase.

Furthermore, by immobilizing the monoclonal antibody of the invention on a solid support (for example a Protein A or Protein G-conjugated Sepharose, agarose or the like resin or a cyanogen bromide-activated Sepharose, agarose or the like resin), a cell isolation column can be constructed. When human bone marrow cells, umbilical cord blood or blood enriched in human hemopoietic stem cells by mobilization with G-CSF is applied onto this column, immature hemopoietic stem cells are retained as adsorbed on the column, thus effecting isolation thereof from other cells.

BEST MODE FOR CARRYING OUT THE INVENTION

The HSCA-3 antigen and the monoclonal antibody which recognizes the antigen, which are provided by the present invention, are now described in further detail. It should, however, be understood that the scope of the invention is by no means delimited by the following examples.

EXAMPLE 1

Preparation of an HSCA-3 Antibody-producing Hybridoma, and Production of HSCA-3 Antibody (a) Sensitizing Antigen As the sensitizing antigen, KG-1 cells (JCRB Cell Bank), which are human myeloblastoid cells derived from an acute myeloid leukemia patient, were used. The KG-1 cells were suspended in 15 ml of 15% fetal calf serum (FCS) -RPMI 1640 medium (product of K. K. Nikken Seibutsu Igaku Kenkyusho) at a final concentration of $1.0 \times 10^5$/ml, sown in a culture dish (product of greiner bio-one) (10 cm dia.), and cultured at 37° C. in a 5% $CO_2$ incubator. On day 4–5 of culture, the cells were harvested by centrifuging (4° C.) at 240 G for 10 minutes and washed twice with PBS(−) (phosphate-buffered saline, pH 7.2; product of K. K. Nikken Seibutsu Igaku Kenkyusho), and $1.0 \times 10^7$ cells were suspended in 200 μl of PBS(−) for use as the sensitizing antigen.

(b) Immunization

As the mouse to be immunized, female BALB/c mice (8 weeks old) were used. The above-mentioned KG-1 cells as the sensitizing antigen was administered subcutaneously to the mice. Then, the like cells ($1.0 \times 10^7$ cells) were administered subcutaneously at day 7, day 14, day 21, day 29, day 54, day 61, day 68, day 74, day 85, and day 92, and as the last immunization, the like cells ($1.0 \times 10^7$ cells) were injected intraperitoneally at day 96.

(c) Preparation of a Hybridoma

Four days after the last immunization, or at day 100 reckoning from the first immunization, the spleen was excised from the mouse, placed in a PBS (−)-containing dish, and ground down by utilizing the ground glass surfaces of two glass slides. The spleen cells were then recovered. The cells were placed in a tube and centrifuged (4° C.) at 240 G for 10 minutes, and the supernatant was discarded.

On the other hand, the counterpart NS-1 cells, which are myeloma cells derived from X63 cells, were prepared as follows. NS-1 cells were adjusted to a concentration of $1.0 \times 10^5$/ml, and suspended in 15 ml of 15% fetal calf serum (FCS)-RPMI 1640 medium, sown in a culture dish (10 cm dia.), and cultured at 37° C. in a 5% $CO_2$ incubator. At day 4–5, the cells were harvested by centrifugation (4° C.) at 240G for 10 minutes. The spleen cells and the NS-1 cells were respectively washed three times with 30 ml of RPMI 1640 medium and the spleen cells (a total of $2.89 \times 10^8$ cells) were admixed with the NS-1 cells (a total of $8.07 \times 10^7$ cells). This mixture was made up to 10 ml with RPMI 1640 medium, placed in a glass tube, and centrifuged (4° C.) at 300 G for 10 minutes, and the supernatant was discarded. To the above glass tube was added 1 ml of PEG solution [a 50% solution of polyethylene glycol 4,000 in PBS(−) (product of Roche Diagnostics) 1 ml+dimethyl sulfoxide 0.1 ml +RPMI 1640 medium 0.1 ml] over 1 minute, followed by stirring for 1 minute. Then, 1 ml of RPMI 1640 medium was added within 1 minute, an additional 1 ml of RPMI 1640 medium added over 1 minute, and finally 7 ml of RPMI 1640 medium added over 3 minutes. The mixture was centrifuged at 150 G for 10 minutes and the supernatant was completely removed.

The pellet obtained was loosened up and a sufficient quantity of 15% FCS-RPMI 1640 medium was added to make a cell concentration of $1 \times 10^7$ cells/ml. The cells were sown on a 96-well flat-bottom plate (product of Corning), 100 μl/well. The following day, a 50-fold concentrated hypoxanthine+aminopterin+thymidine (HAT) solution (product of Dainippon Pharmaceutical) was diluted to 2% concentration with 15% FCS-RPMI 1.640 medium (HAT 2% solution) and added, 100 μl/well, and further on the following day, a 100 μl portion of the medium was replaced with 100 μl of the above HAT 2% solution. Similarly, at day 3, day 5, day 8, day 11, and day 14 following cell fusion, 100 μl of the medium in the well was replaced with 100 μl of said HAT 2% solution. Then, the antibody activity in the culture supernatant was assayed by the following ELISA method.

(d) Antibody Assay by an ELISA Method

A poly-L-lysine-treated 96-well ELISA plate was prepared as follows.

Using an EIA/RIA high-binding flat-bottom plate (product of Coaster) as the 96-well plate for ELISA, 50 μl of poly-L-lysine solution (50 μg/ml) was added to each well of the plate. After stirring with a plate mixer, the plate was left standing at room temperature for 5–30 minutes and the poly-L-lysine solution was aspirated off. Further, for washing, 100 μl of sterilized ultra-pure water was added to each well of the plate and, then, aspirated off. This washing operation was repeated further twice and the plate was then allowed to stand and dry in a clean bench. The above procedure made a poly-L-lysin-treated 96-well ELISA plate ready for use. Then, the KG-1 cells used as the immunogen ($4.8 \times 10^6$ cells/96-well plate) were washed with 3 portions of Erle's buffer salt solution (EBSS) (product of K. K. Nikken Seibutsu Igaku Kenkyusho), adjusted to a cell concentration of $1 \times 10^6$ cells/ml with PBS (−), and distributed into the plate, 50 μl/well. The plate was allowed to stand at room temperature for 15 minutes to let the cells adhere to the bottom, after which it was centrifuged at 90 G. After the supernatant was aspirated off, 0.05% glutaraldehyde-PBS (−) was gently added to the plate, 50 μl/well, and after standing for 3 minutes at room temperature, 100 μl of PBS (−) was added to each well and aspirated off. After the wells were further washed with 3 portions of PBS (−), 100 μl of blocking solution (0.2% gelatin, 0.1% BSA, 100 mM glycine, 0.1% sodium azide/PBS (−)) was added to each well and aspirated off. Once again, 100 μl of blocking solution was added to each well and, after 1 hour of standing at room temperature, aspirated off. Then, 100 μl of the culture supernatant of the hybridoma was placed in each well and reacted at room temperature for at least 2 hours. The wells were washed with three 150 μl portions of 0.1% gelatin-supplemented PBS (−)–0.05% Tween 20 solution.

Then, 100 μl of a 1,500-fold dilution of goat IgG antibody (antibody to mouse IgG, IgA, IgM; product of Kappel) was added to each well and reacted at room temperature for at least 1 hour. Then, the wells were washed 3 times using 150 μl of 0.1% gelatin-supplemented PBS-0.05% Tween 20 solution. o-Phenylenediamine (OPD)-hydrogen peroxide solution (a solution of 0.3% OPD and 0.02% hydrogen peroxide in 0.05 M citrate buffer (pH 4.0)) was added, 100 μl/well, and after standing at room temperature for 10 minutes and confirmation of color development, 100 μl/well of 1N sulfuric acid-2 mM sodium azide solution was further added, followed by stirring. Finally, the absorbance at the wavelength of 492 nm (OD 492) was measured with a plate reader (product of Dainippon Pharmaceutical) to determine the amount of colored pigment and the antibody activity was estimated. As a positive control, a 500-fold PBS (−) dilution of the serum of the mouse immunized with KG-1 cells prior to harvesting of spleen cells, and as a negative control, a 500-fold PBS (−) dilution of normal mouse serum was used. The OD492 of the HSCA-3 antibody culture supernatant was 0.195, the OD 492 of the negative control was 0.019, and the OD 492 of the positive control was 0.453.

(e) Single Cell Cloning

The monoclonal antibody HSCA-3 having KG-1 cell-binding activity as obtained above in Example 1 (d) was subjected to single cell cloning by the limiting dilution method. Thus, the hybridoma was suspended in cloning medium [15% FCS-RPMI 1640 medium supplemented with 5% (w/w) of Briclone (product of Dainippon Pharmaceutical)] at a concentration of 1 cell/well, and the resulting suspension was distributed, 100 μl/well, into a 96-well flat-bottom plate (product of Corning) seeded with thymocytes as feeder cells and cultured in the presence of 5% $CO_2$ at 37° C. The feeder cells were prepared in the following manner. From BALB/c mice, the thymus was excised and the cells were loosened up by pipetting and suspended in 15% FCS-RPMI 1640 medium containing hypoxanthine/thymidine (HT). The cell suspension was adjusted to a concentration of $5 \times 10^6$ cells/ml and distributed, 100 μl/well. After about 2 weeks, 100 μl of the culture supernatant containing a single hybridoma cell was recovered and checked for antibody activity by the antibody assay using the above ELISA method (d). Thus, the positive clone was subjected to the same single cell cloning as above for a total of 5 times and the hybridoma clone showing stable antibody production and unmistakably producing HSCA-3 antibody was obtained. This HSCA-3 antibody-producing hybridoma has been deposited under Budapest treaty on May 20, 2002 with National Institute of Advanced Industrial Science and Technology, International Patent Organism Depositary as Mouse-Mouse Hybridoma HSCA-3. The accession number is FERM BP-8045. This international deposit was transferred from original deposit P-17789 (date of original deposit Mar. 16, 2000).

(f) Large-scale Preparation and Purification of HSCA-3 Antibody

For large-scale preparation of HSCA-3 antibody, the hybridoma was injected intraperitoneally in mice to prepare an asites containing a large amount of HSCA-3 antibody. Thus, $1 \times 10^7$ cells/ml PBS (−) of the HSCA-3 hybridoma was administered intraperitoneally to BALB/c mice and in 1–2 weeks when the mouse abdomen had hypertrophied with the production of ascites reaching a maximum, 10.0 ml of the ascites was harvested. After addition of an equal volume (10.0 ml) of PBS (−) and, then, an equal volume (20.0 ml) of SAS solution (75 g of ammonium sulfate was dissolved in 100 ml of pure water under warming at 50° C., the solution was allowed to stand at 4° C. overnight, the excess ammonium sulfate was removed by precipitation, and the supernatant was used) was further added and the whole mixture was left standing on ice for 30–60 minutes. After centrifugation (4° C.) at 8,000 G for 10 minutes, 4.0 ml of PBS (−) was added for suspending the precipitate, 1 ml of SAS solution was also added, and the mixture was allowed to stand on ice for 30–60 minutes. After centrifugation (4° C.) at 8,000 G for 10 minutes, 2.55 ml of SAS solution was added to the supernatant (33% saturation) and the mixture was allowed to stand on ice for 30–60 minutes. After centrifugation (4° C.) at 8,000 G for 10 minutes, the precipitate was recovered and dissolved in 4.0 ml of PBS (−). The solution was dialyzed against 3L of PBS (−) at 4° C. Of 46.6 mg (4 ml as solution) of the antibody purified by this ammonium sulfate isolation, about 10 mg was further purified using 2 ml of Protein G-Sepharose (product of Amersham Pharmacia Biotech). After the Protein G-Sepharose column was equilibrated with 10 ml of binding buffer (MAPS II kit, Nippon Bio-Rad Laboratories), the antibody sample was applied onto the column and washed with 30 ml of binding buffer. Elution from the column was carried out with 10 ml of 0.2 M glycine/HCl (pH 2.2). The protein concentration of the antibody solution recovered using a Coomassie Brilliant Blue Assay Kit (product of Nippon Bio-Rad Laboratories) was 0.35 mg/ml or a total of 2.8 mg.

EXAMPLE 2

Determination of the Antibody's Subclass

Using an ELISA technique, the immunoglobulin class and subclass of the HSCA-3 antibody was determined. For this purpose, a mouse hybridoma subtyping kit (product of Roche Diagnostics) was used. The anti-mouse immunoglobulin (derived from sheep) was diluted 500-fold with coating buffer (50 mM sodium carbonate buffer/0.01% sodium azide (pH 9.4–9.7), distributed in a 96-well flat-bottom plate, 50 μl per well, and allowed to stand at 37° C. for 30 minutes. Then, the plate was washed with 200 μl/well of wash solution (0.9% sodium chloride/0.1% Tween 20) twice. The plate was allowed to stand in post-coating buffer (the peptide obtained by the degradation of gelatin was dissolved with Tris-HCl buffer and sodium chloride), 200 μl/well, at 37° C. for 15 minutes and, then, washed twice with 200 μl/well of wash solution. Then, 50 μl/well of the HSCA-3 antibody culture supernatant was applied and, after standing at 37° C. for 30 minutes, the plate was washed twice with 200 μl/well of wash solution. Further, the sub-class-specific anti-mouse immunoglobulin-peroxidase (POD) conjugates (anti-mouse IgG, IgG1, IgG2a, IgG2b, IgG3, IgM, IgA, lambda chain, kappa chain) were diluted 10-fold and applied, 50 μl/well. After standing for 30 minutes at 37° C., the plate was washed twice with 200 μl/well of wash solution. The substrate solution [one 2,2'-azinobis(3-ethylbenzothiazoline-6-sulfonic acid) (ABTS) tablet was dissolved in 5 ml of substrate buffer (the perborate dissolved in citric acid/sodium phosphate buffer)] was applied, 100 μl/well, and the reaction was carried out at room temperature for not longer than 30 minutes. When the positive control sample (anti-mouse IgG1) had assumed a dark green color, 4 mM sodium azide solution was added, 100 µl/well, to stop the reaction. The absorbance at 405 nm was measured for each well of the plate with a spectrophotometer (U2000; Hitachi, Ltd.).

The results were as follows. The positive control sample (IgG1, kappa chain) gave an absorbance at 405 nm of 1.422 for anti-mouse IgG, 2.525 for anti-mouse IgG1, 0.087 for anti-mouse IgG2a, 0.049 for anti-mouse IgG2b, 0.063 for anti-mouse IgG3, 0.064 for anti-mouse IgM, 0.057 for anti-mouse IgA, 0.077 for lambda chain, and 0.572 for kappa chain. In contrast, the negative control sample gave an absorbance at 405 nm of 0.109 for anti-mouse IgG, 0.126 for anti-mouse IgG1, 0.093 for anti-mouse IgG2a, 0.052 for anti-mouse IgG2b, 0.060 for anti-mouse IgG3, 0.079 for anti-mouse IgM, 0.061 for anti-mouse IgA, 0.058 for lambda chain, and 0.122 for kappa chain. The HSCA-3 antibody gave an absorbance at 405 nm of 1.737 for anti-mouse IgG, 2.550 for anti-mouse IgG1, 0.086 for anti-mouse IgG2a, 0.047 for anti-mouse IgG2b, 0.056 for anti-mouse IgG3, 0.065 for anti-mouse IgM, 0.057 for anti-mouse IgA, 0.059 for lambda chain, and 0.325 for kappa chain. Thus, the immunoglobulin class and subclass of HSCA-3 antibody is IgG1 and the type of the light chain (L chain) is kappa chain.

EXAMPLE 3

Immunoprecipitation Analysis of HSCA-3 Antibody-reactive Antigen

From a culture of KG-1 cells in 15% FCS-RPMI 1640 medium, $5.0 \times 10^7$ cells in the logarithmic phase of growth were collected and washed with 3 portions of PBS (−). The cell pellet was collected in a 15 ml polypropylene tube (product of Falcon), suspended by adding 150 µl of PBS (−), and allowed to stand on ice. This suspension was adjusted to 30° C. in an incubator prior to using. To this tube, 50 µl of lactoperoxidase (product of Sigma; dissolved in PBS(−) to 2 mg/ml) and 10 µl of 0.5 M phosphate buffer (about 3–4 ml of 0.5 M sodium dihydrogenphosphate was added to 1.95 ml of 0.5 M sodium dihydrogenphosphate to make pH 7.0) were added. Further, about 1 mCi equivalent of Na $^{125}$I (product of NEN; low pH, total 2 mCi) was added and, without delay, 20 µl of aqueous hydrogen peroxide solution (30% hydrogen peroxide diluted 1,000-fold with PBS (−)) was added and mixed. The mixture was incubated at 30° C. for 4 minutes. Then, 20 µl of aqueous hydrogen peroxide solution (30% hydrogen peroxide diluted 1,000-fold with PBSC (−)) was further added and mixed. The mixture was allowed to stand at room temperature for 10 minutes. Then, 5 ml of wash buffer cooled to 4° C. (0.02% sodium azide/2 mM potassium iodide/PBS(−)) was added and, at room temperature, the whole was centrifuged at 300 G for 7 minutes. This washing procedure was repeated three times. A centrifuge tube was charged with 2 ml of fetal calf serum and a suspension of cells in 1 ml of wash buffer was gently layered on the serum and centrifuged at 300 G for 10 minutes. The pellet obtained was washed with 2 portions of wash buffer. To this centrifugal pellet of Na $^{125}$I-labeled cells was added 0.5 ml Nonidet P (NP) -40 buffer [NP-40 1 g, Tris-HCl 0.12 g, NaCl 0.87 g, and sodium azide 0.02 g were put in 80 ml of distilled water, adjusted to pH 7.2 with HCl, and made up to 100 ml], followed by mixing with a vortex mixer (allowed to stand on ice for 15 minutes). This was centrifuged at 10,000 G for 20 minutes and the supernatant was recovered. Of this extract of Na $^{125}$I-labeled KG-1 cells (total 500 µl), a 80 µl portion was taken and 1.5 pg of HSCA-3 antibody or 1.5 µg of control IgG1 antibody (product of Immunotech) was added, followed by standing for 30 minutes on ice. On the other hand, after Protein G-Sepharose was washed with 3 portions of NP-40 buffer, 10 ml of NP-40 buffer was added to 10 ml of this Protein G-Sepharose, and a 20 µl portion was added to the above KG-1 cell extract containing the antibody, followed by 1 hour of incubation on ice. Then, 1 ml of NP-40 buffer was added, the whole was centrifuged at 8,000 G for 3 minutes, and the supernatant was discarded. This washing procedure was repeated another 4 times. To this was added 30 µl of SDS-polyacrylamide gel electrophoresis sample solvent buffer (150 mM Tris-HCl (pH 6.8), 4% SDS, 14% glycerol), and a 15 µl aliquot was subjected to SDS-polyacrylamide gel electrophoresis. An SDS-polyacrylamide gel (10% polyacrylamide gel) was prepared and the above 15 µl sample was applied. The control CD34 (Class III) antibody (product of Immunotech) was applied to lane 1 and the HSCA-3 antibody was applied to lane 2. To lane 3, 5 µl of Bench Mark Prestained Protein Ladder (product of Gibco/BRL) was applied. After 1 hour of electrophoresis at a constant voltage of 100V, the gel was fixed with 50% trichloroacetic acid for 30 minutes and washed with 3 portions of distilled water, for 30 minutes each. The migration position of the standard protein was confirmed and the gel was dried with a gel dryer and subjected to autoradiography. The results are presented in FIG. 1.

The CD34 (Class III) antibody shows abroad band, reacting with a protein having a molecular weight of $105–120 \times 10^3$. In contrast, HSCA-3 antibody reacted with a protein having a molecular weight of about $110 \times 10^3$.

EXAMPLE 4

Expression of HSCA-3 Antigen in KG-1 Cells

KG-1 cells, $1 \times 10^5$, were placed in 3 tubes and respectively washed with 2 portions of PBS (−) (containing FCS 1%, sodium azide 0.01%). Then, the first tube (A) was charged with IgG1-FITC antibody [FITC-labeled IgG1 antibody (product of Immunotech)] and IgG1-PE antibody [phycoerythrin (PE)-labeled IgG1 antibody (product of Immunotech)] and the second tube (B) was charged with CD34 (Class III) -FITC antibody (product of Immunotech) and CD38-PE antibody (product of Immunotech), 0.5 µg each, followed by stirring and 30 minutes' standing on ice. Each tube was washed with 2 portions of PBS (−) (containing FCS 1%, sodium azide 0.01%) and, then, propidium iodide (product of Sigma-Aldrich Japan) was added at a final concentration of 10 µg/ml to stain the cells. The third tube (C) was charged with 0.5 µg of HSCA-3 antibody and left standing on ice for 30 minutes. After the tube was washed with 2 portions of PBS (−) (containing FCS 1% and sodium azide 0.01%), 50 µl of a 2,500-fold PBS(−) (containing FCS 1%, sodium azide 0.01%) dilution of FITC-labeled anti-mouse Ig antibody (product of Nordic Labs.) was added, followed by standing on ice for 30 minutes. It was then washed with PBS (−) (FCS 1%, sodium azide 0.01% added) once. Further, 50 µl of a 50-fold dilution of normal mouse serum (product of Rockland) in PBS(−) (FCS 1%, sodium azide 0.01% added) was added, and the tube was allowed to stand on ice for 15 minutes. Then, 0.5 µl of CD-38-FE antibody was added, and the tube was allowed to stand on ice for 30 minutes. It was washed with 2 portions of PBS (−) (FCS 1%, sodium azide 0.01%) and, then, propidium iodide was added at a final concentration of 10 µg/ml to stain the cells.

The stained cells were assayed with the flow cytometer FACScan (manufactured by Becton Dickinson) at an exciting wavelength of 488 nm and a maximum fluorescent wavelength of 530 nm. The results are presented in FIG. 2. In the view, (A), (B) and (C) represent the results corresponding to the above tubes (A), (B) and (C), respectively.

Figure 2:
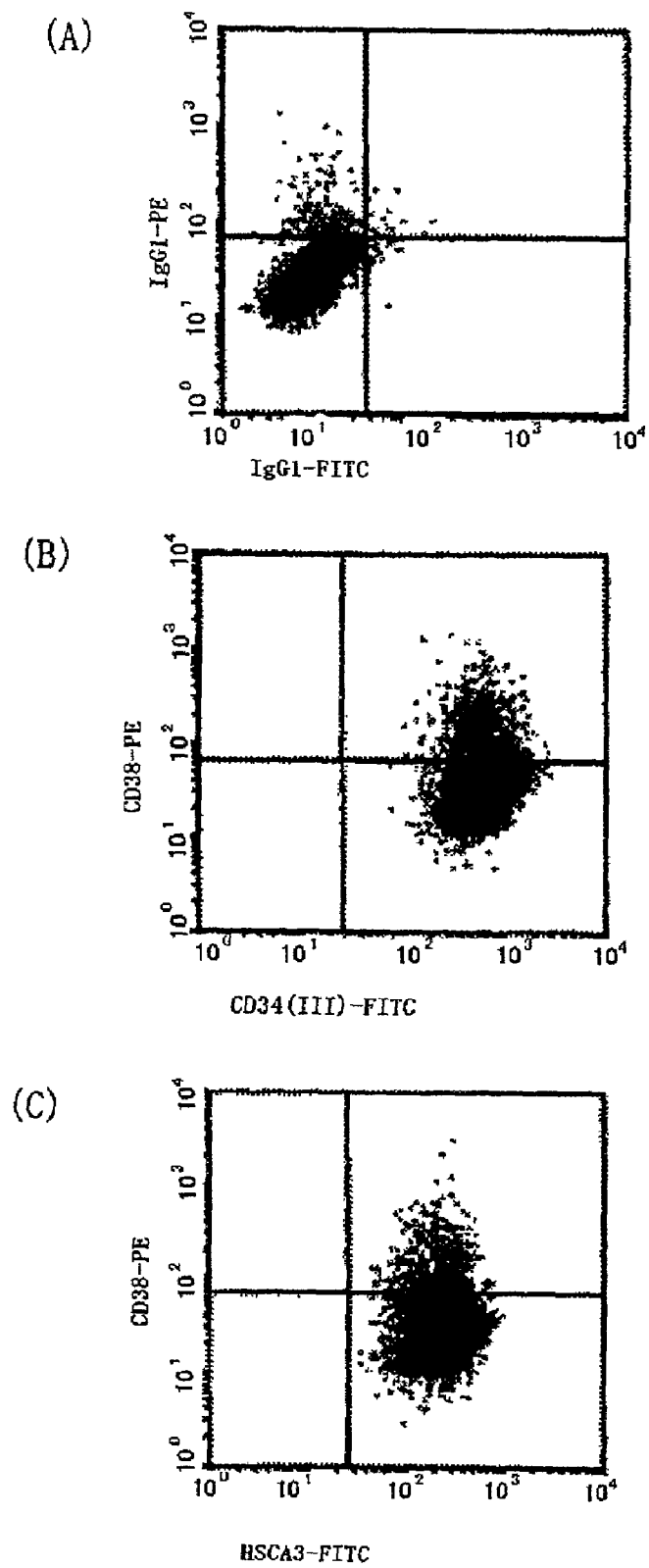
FIG. 2 is a flow cytometry chart showing the expression of HSCA-3 antigen in KG-1 cells.

Referring to FIG. 2 (A), the abscissa represents the fluorescent intensity of mouse IgG1-FITC antibody, while the ordinate represents the fluorescent intensity of mouse IgG1-PE antibody. The crossed lines are the positive-negative test lines drawn along the ordinate and abscissa of the flow cytometry chart obtained by treatment with mouse IgG1-FITC antibody and mouse IgG1-PE antibody. Each dot represents a cell. Similarly, referring to FIG. 2 (B), the bottom right quadrant represents CD34 (Class III)$^+$CD38$^-$, the top right quadrant represents CD34 (Class III)$^+$CD38$^+$, the top left quadrant represents CD34 (Class III)$^-$CD38$^+$, and the bottom left quadrant represents CD38 (Class III)$^-$CD38$^-$. It is apparent from the results that KG-1 cells belong to CD34 (Class III)$^+$. Similarly, from the results illustrated in FIG. 2 (C), it can be seen that KG-1 cells are HSCA-3$^+$. A similar experiment was performed using CD34-FITC antibodies which would recognize other classes of CD34 molecule in lieu of CD34 (Class III)-FITC antibody, that is to say CD34 (Class I)-FITC antibody and CD34 (Class II)-FITC antibody, respectively. As a result, like CD34 (Class III)-FITC antibody, these antibodies were capable of recognizing KG-1 cells.

EXAMPLE 5

Expression of HSCA-3 Antibody in CD34$^+$ Jurkat Cells

Figure 3:
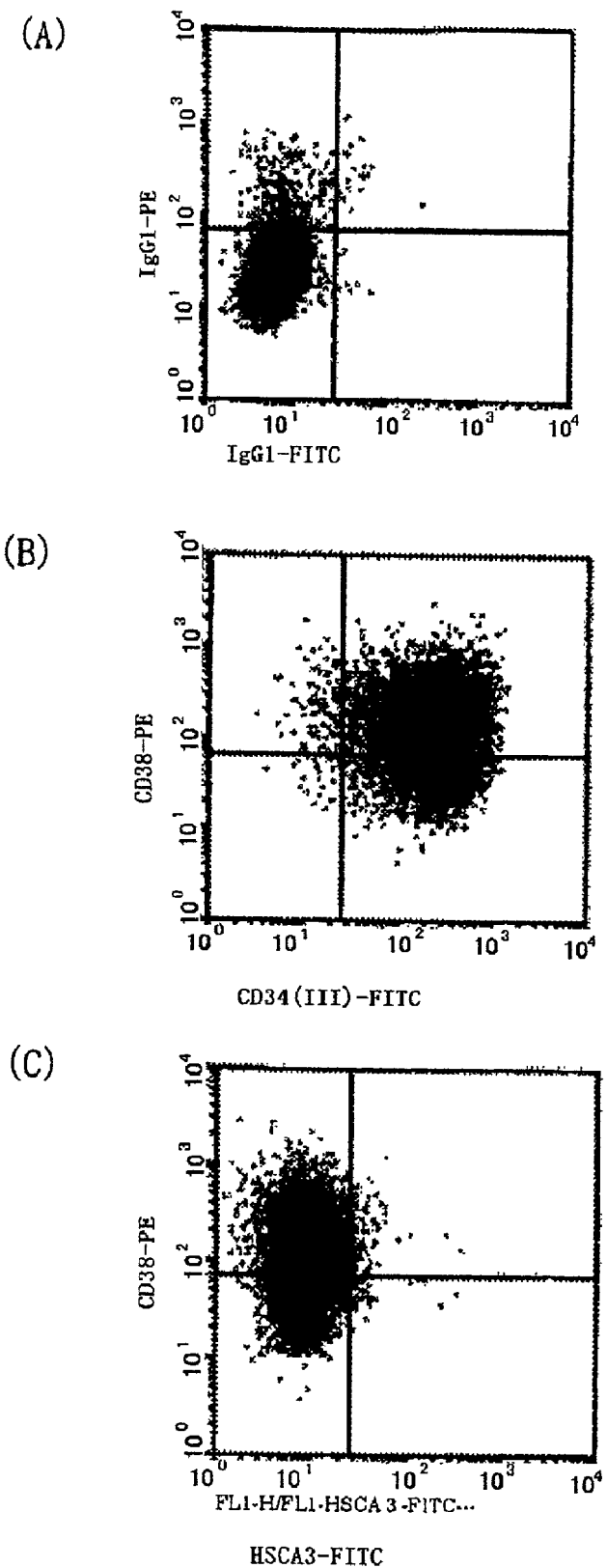
FIG. 3 is a flow cytometry chart showing the expression of HSCA-3 antigen in CD34$^+$ Jurkat cells.

CD34$^+$ Jurkat cells, 1×10$^5$ cells, were put in 3 tubes and washed with 2 portions of PBS(−) (FCS 1%, sodium azide 0.01% added). Then, the first tube (A) was charged with 0.5 µg each of IgG1-FITC antibody and IgG1-PE antibody and the second tube (B) with 0.5 µg each of CD34 (Class III)-FITC antibody and CD38-PE antibody, followed by stirring, and each tube was allowed to stand on ice for 30 minutes. After washing twice with PBS (−) (FCS 1%, sodium azide 0.01% added), propidium iodide (Sigma-Aldrich Japan) was added at a final concentration of 10 µg/ml to stain the cells. The third tube (C) was charged with 0.5 Vg of HSCA-3 antibody and allowed to stand on ice for 30 minutes. After washing twice with PBS (−) (FCS 1% sodium azide 0.01% added), 50 µl of a 2,500-fold dilution of FITC-labeled anti-mouse Ig antibody in PBS(−) (FCS 1% sodium azide 0.01% added) was added. The tube was allowed to stand on ice for 30 minutes and washed with PBS(−) (FCS 1% sodium azide 0.01% added) once. Further, 50 µl of a 50-fold dilution of normal mouse serum in PBS(−) (FCS 1% sodium azide 0.01% added) was added and the tube was allowed to stand on ice for 15 minutes. Then, 0.5 µg of CD38-PE antibody was added and the tube was allowed to stand on ice for 30 minutes. After washing twice with PBS (−) (FCS 1% sodium azide 0.01% added), propidium iodide was added at a final concentration of 10 µg/ml to stain the cells. The stained cells were assayed by means of flow cytometer FACScan. The results are presented in FIG. 3. In the view, (A), (B) and (C) represent the results corresponding to the above tubes (A), (B) and (C), respectively.

Referring to FIG. 3(A), the abscissa represents the fluorescent intensity of mouse IgG1-FITC antibody and the ordinate represents the fluorescent intensity of mouse IgG1-PE antibody. Using the results as a reference, positive-negative test lines were drawn along the ordinate and abscissa of the flow cytometry chart. It is apparent from the image in FIG. 3(B) that CD34$^+$ Jurkat cells are CD34 (Class III)$^+$. From FIG. 3(C), it is apparent that CD34$^+$ Jurkat cells are HSCA-3$^-$. A similar experiment was performed using CD34-FITC antibodies which recognize other classes of CD34 molecule in lieu of CD34 (Class III)-FITC antibody, that is to say CD34 (Class I)-FITC antibody and CD34 (Class II) -FITC antibody. As a result, like CD34 (Class III)-FITC antibody, these antibodies were capable of recognizing CD34$^+$ Jurkat cells.

EXAMPLE 6

Expression of HSCA-3 Antigen in Various Cell Lines

Using cell lines other than KG-1 cells and CD34$^+$ Jurkat cells, namely (1) KU812, (2) KU812 (CD34$^+$), (3) HEL, (4) Jurkat (CD2$^+$CD34$^-$), (5) MOLT14, (6) MOLT4, (7) RAJI, (8) NALM6, (9) DAUDI, (10) K562, (11) THP-1, (12) HL60, (13) U937 and (14) NS-1, the staining with HSCA-3 antibody was carried out. To 1×10$^5$ cells each of the above cell lines, 0.5 µg of HSCA-3 antibody was respectively added, and each system was allowed to stand on ice for 30 minutes. After washing twice with PBS(−) (FCS 1% sodium azide 0.01% added), 50 µl of a 2,500-fold dilution of FITC-labeled anti-mouse Ig antibody in PBS (−) (FCS 1% sodium azide 0.01% added) was added, and the system was allowed to stand on ice for 30 minutes and, then, washed with PBS(−) (FCS 1% sodium azide 0.01% added) once. Further, 50 µl of a 50-fold dilution of normal mouse serum in PBS (−) (FCS 1% sodium azide 0.01% added) was added and the mixture was allowed to stand on ice for 15 minutes. After washing twice with PBS(−) (FCS 1% sodium azide 0.01% added), propidium iodide was added at a final concentration of 10 µg/ml to stain the cells. The stained cells were assayed by flow cytometer FACScan.

The results were as follows.

(1) KU812=+
(2) KU812 (CD34$^+$)=++
(3) HEL=+
(4) Jurkat (CD2$^+$CD34$^-$)=−
(5) MOLT14=−
(6) MOLT4=−
(7) RAJI=−
(8) NALM6 =−
(9) DAUDI=−
(10) K562=−
(11) THP-1=−
(12) HL60=−
(13) U937=−
(14) NS-1=−

In the above list, ++ means strongly positive, + weekly positive, − negative.

The cells showing a positive response to CD34 antibody was positive to HSCA-3 antibody, too. Considering this in conjunction with the results of Example 5, the difference between CD34 antibody and HSCA-3 antibody is that whereas CD34 antibody is able to recognize CD34$^+$ Jurkat cells, HSCA-3 antibody does not recognize them.

EXAMPLE 7

Labeling of HSCA-3 Antibody with Biotin-hydrazide

HSCA-3 antibody, 2.27 mg, was dialyzed against 0.1 M sodium acetate buffer (pH 5.5) overnight and 20 mM sodium periodate was then added at a final concentration of 10 mM, followed by stirring on ice for 20 minutes. To each ml of the total reaction mixture, 11 μl of 10% glycerol solution was added and after stirring for 5 minutes, the whole was dialyzed against 0.1 M sodium acetate buffer (pH 5.5) at room temperature overnight. Biotin-hydrazide powder was added at a final concentration of 10 mM and the mixture was kept stirring at room temperature for 2 hours and then centrifuged at 1,200 G for 10 minutes. The precipitate was discarded. The supernatant was dialyzed against PBS (−) (supplemented with sodium azide 0.01%) for one day to give a labeled antibody.

EXAMPLE 8

Expression of HSCA-3 Antigen and CD34 Antigen in Umbilical Cord Blood Monocytes.

Umbilical cord blood monocytes were prepared as follows. Thus, a 15 ml polypropylene tube (product of Coming) was charged with 0.05 ml of heparin sodium injection (10,000 U/ml) to which 4 ml of human umbilical cord blood, a donation with informed consent from Department of obstetrics and gynecology, was added. Then, 5 ml of PBS (−)/H [1% heparin sodium injection (1,000 U/ml) was added to PBS(−)] was added and the whole was thoroughly stirred. Then, 3.5 ml of lymphocyte separation medium (product of Organon Teknika) was placed on the tube bottom and the mixture was centrifuged at 400 G for 30 minutes. The monocyte layer was gathered, and PBS(−)/HF [1% heparin sodium injection (1,000 U/ml) and 2.5% FCS were added to PBS(−)] was added to a 15 ml polypropylene tube to make 15 ml, and centrifuged at 510 G for 10 minutes. The precipitate was suspended by adding 15 ml of PBS(−)/HF and recentrifuged at 240 G for 10 minutes. The resulting precipitate was suspended in 0.5 ml of 10% FCS/RPMI 1640 and adjusted to a cell number of about $1 \times 10^7$ cells/ml. To this was added 0.5 ml of a medium for frozen storage (20% dimethyl sulfoxide (DMSO)/10% FCS-RPMI 1640) and the resulting suspension was stored frozen in liquid nitrogen. This was thawed when needed, washed with 15% FCS-RPMI 1640, and put to use.

Umbilical cord blood monocytes, $1 \times 10^6$ cells, were distributed in 3 tubes. The first tube (A) was charged with IgG1-FITC antibody and IgG2-PE antibody (product of Immunotech) and the second tube (B) with CD34 (Class II)-FITC antibody (product of Immunotech) and CD34 (Class III)-PE antibody (product of Immunotech), 0.5 μg each, and after stirring, each tube was allowed to stand on ice for 30 minutes. After washing twice with PBS(−) (FCS 1%, sodium azide 0.01% added), propidium iodide was added at a final concentration of 10 μg/ml to stain the cells. The third tube (C) was charged with 5 μg of HSCA-3 antibody labeled with biotin-hydrazide and allowed to stand on ice for 30 minutes. After washing twice with PBS(−) (FCS 1%, sodium azide 0.01% added), 1 μg of FITC-labeled avidin (product of Becton Dickinson) was added and the tube was allowed to stand on ice for 30 minutes. After washing twice with PBS(−) (FCS 1%, sodium azide 0.01% added), CD34 (Class III)-PE antibody was added, 0.5 μg each, and after stirring, the tube was allowed to stand on ice for 30 minutes. After washing twice with PBS(−) (FCS 1%, sodium azide 0.01% added), propidium iodide was added at a final concentration of 10 μg/ml to stain the cell. The stained cells were assayed by means of flow cytometer FACScan. The results are presented in FIG. 4. In the view, (A), (B) and (C) represent the results corresponding to the above tubes (A), (B) and (C), respectively.

Figure 4:
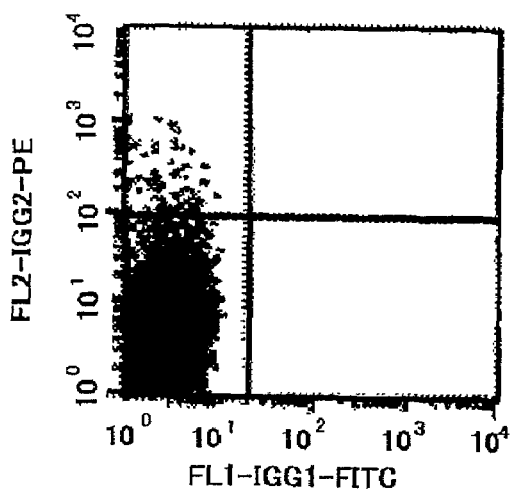
FIG. 4 is a flow cytometry chart showing the expression of HSCA-3 antigen and CD34 antigen in umbilical cord blood monocytes.
Figure 4:
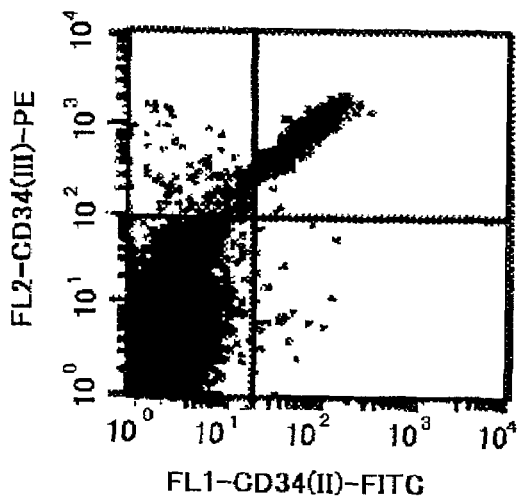
Figure 4:
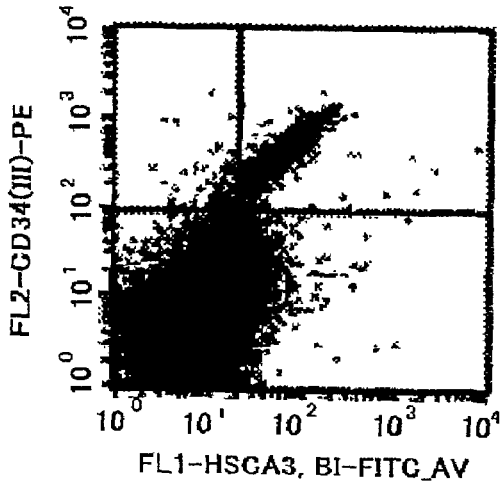

Referring to FIG. 4 (A), the abscissa represents the fluorescent intensity of mouse IgG1-FITC antibody and the ordinate represents the fluorescent intensity of mouse IgG2-PE antibody. The positive-negative test lines were drawn along the ordinate and abscissa of the flow cytometry chart. Referring to FIG. 4 (B), the ordinate represents the fluorescent intensity of CD34 (Class III)-PE antibody and the abscissa represents the fluorescent intensity of CD34 (Class II)-FITC antibody. As a result, neither a CD34 (Class II)$^+$CD34 (Class III)$^-$-fraction nor a CD34 (Class III)$^+$CD34 (Class II)$^-$fraction was detected in the umbilical cord blood monocytes. Referring to FIG. 4 (C), the ordinate represents the fluorescent intensity of CD34 (Class III)-PE antibody and the abscissa represents the fluorescent intensity of HSCA-3 antibody (FITC-avidin conjugation). As a result, an HSCA-3$^+$CD34 (Class III) fraction was found to exist in umbilical cord blood monocytes. Therefore, HSCA-3 antibody is considered to recognize an antigen different from the antigen recognized by CD34 (Class III) antibody.

The invention claimed is:

1. A monoclonal antibody which recognizes human immature hemopoietic stem cells but does not recognize CD34$^+$ Jurkat cells, and
    which binds to the same antigen as does the monoclonal antibody produced by a hybridoma having an accession number of FERM BP-8045.

2. A solid support comprising the antibody according to claim 1 as immobilized thereon.

3. An immunoreactive fragment of the antibody according to claim 1.

4. The immunoreactive fragment according to claim 3, which is fluorescent-labeled, radioisotope-labeled, or enzyme-labeled.

5. A solid support comprising the immunoreactive fragment according to claim 3 as immobilized thereon.

6. A hybridoma which has an accession number of FERM BP-8045.

7. The hybridoma according to claim 6,
    which is acquired by the fusion of antibody-producing cells of a mammal immunized with KG-1 cells, which are human myeloblastoid cells derived from an acute myeloid leukemia patient, to myeloma cells.

8. The monoclonal antibody according to claim 1, as produced by a hybridoma having an accession number of FERM BP-8045.

9. The antibody according to claim 1, which is fluorescent-labeled, radioisotope-labeled, or enzyme-labeled.

10. The antibody according to claim 8, which is fluorescent-labeled, radioisotope-labeled, or enzyme-labeled.

* * * * *